US006892092B2

(12) United States Patent
Palreddy et al.

(10) Patent No.: US 6,892,092 B2
(45) Date of Patent: May 10, 2005

(54) CARDIAC RHYTHM MANAGEMENT SYSTEM WITH NOISE DETECTOR UTILIZING A HYSTERESIS PROVIDING THRESHOLD

(75) Inventors: Surekha Palreddy, Vadnais Heights, MN (US); Carlos Ricci, Apple Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 392 days.

(21) Appl. No.: 10/046,650

(22) Filed: Oct. 29, 2001

(65) Prior Publication Data

US 2003/0083713 A1 May 1, 2003

(51) Int. Cl.[7] ............................................. A61B 5/0402
(52) U.S. Cl. ...................................... 600/509; 128/901
(58) Field of Search ............................. 600/509, 521; 607/2, 27, 62; 128/901, 902

(56) References Cited

U.S. PATENT DOCUMENTS

| 4,432,362 A | | 2/1984 | Leckrone et al. ...... 128/419 PG |
| 4,589,420 A | * | 5/1986 | Adams et al. ............... 600/515 |
| 4,679,144 A | * | 7/1987 | Cox et al. .................... 600/516 |
| 4,779,617 A | | 10/1988 | Whigham ............... 128/419 P |
| 4,913,146 A | | 4/1990 | DeCote, Jr. .................. 128/419 |
| 4,960,123 A | * | 10/1990 | Maker ............................. 607/4 |
| 5,010,887 A | | 4/1991 | Thornander ................. 128/696 |
| 5,188,117 A | | 2/1993 | Steinhaus et al. ........... 128/708 |
| 5,209,237 A | | 5/1993 | Rosenthal .................... 128/698 |
| 5,492,128 A | | 2/1996 | Wickham .................... 128/696 |
| 5,522,857 A | | 6/1996 | van Krieken ................... 607/9 |
| 5,562,713 A | | 10/1996 | Silvian ......................... 607/32 |
| 5,564,430 A | | 10/1996 | Jacobson et al. ........... 128/697 |
| 5,573,550 A | | 11/1996 | Zadeh et al. .................. 607/28 |
| 5,591,214 A | | 1/1997 | Lu .................................. 607/9 |
| 5,613,495 A | | 3/1997 | Mills et al. .................. 128/696 |
| 5,647,379 A | | 7/1997 | Meltzer ....................... 128/891 |
| 5,697,958 A | | 12/1997 | Paul et al. ..................... 607/31 |
| 5,702,425 A | | 12/1997 | Wickham ....................... 607/9 |
| 5,702,427 A | | 12/1997 | Ecker et al. ................... 607/28 |
| 5,709,215 A | | 1/1998 | Perttu et al. ................. 128/708 |
| 5,755,738 A | | 5/1998 | Kim et al. ...................... 607/9 |
| 5,766,227 A | | 6/1998 | Nappholz et al. .............. 607/9 |
| 5,778,881 A | | 7/1998 | Sun et al. .................... 128/696 |
| 5,782,876 A | | 7/1998 | Flammang ..................... 607/4 |
| 5,792,212 A | | 8/1998 | Weijand ........................ 607/73 |
| 5,817,130 A | | 10/1998 | Cox et al. ....................... 607/5 |
| 5,817,135 A | | 10/1998 | Cooper et al. ................ 607/17 |
| 5,861,008 A | * | 1/1999 | Obel et al. .................... 607/11 |
| 5,865,749 A | | 2/1999 | Doten et al. ................ 600/443 |
| 5,867,361 A | | 2/1999 | Wolf et al. .................. 361/302 |

(Continued)

FOREIGN PATENT DOCUMENTS

WO    WO-01/43820    6/2001    ............ A61N/1/37

OTHER PUBLICATIONS

Gunderson, Bruce., "Automatic Identification of ICD Lead Problems Using Electrograms", PACE, vol. 24, p. 664, APr. 2002, (2002), 664.

*Primary Examiner*—Kennedy Schaetzle
(74) *Attorney, Agent, or Firm*—Schwegman, Lundberg, Woessner & Kluth, P.A.

(57) ABSTRACT

A system, method, or device determines whether noise is present on a sampled and/or digitized sensed intrinsic cardiac signal based on a moving count of turning/inflection points of the signal. If noise is detected, the manner in which the cardiac signal is acquired, or the manner in which the device operates in response to the acquired cardiac signal (or both) is altered to reduce the risk of erroneously detecting noise as a heart depolarization and, therefore, inappropriately triggering or withholding therapy.

27 Claims, 11 Drawing Sheets

U.S. PATENT DOCUMENTS

| | | | |
|---|---|---|---|
| 5,870,272 A | 2/1999 | Seifried et al. | 361/302 |
| 5,871,509 A | 2/1999 | Noren | 607/9 |
| 5,891,171 A | 4/1999 | Wickham | 607/4 |
| 5,897,575 A | 4/1999 | Wickham | 607/4 |
| 5,957,857 A * | 9/1999 | Hartley | 600/521 |
| 5,978,710 A | 11/1999 | Prutchi et al. | 607/17 |
| 5,999,848 A | 12/1999 | Gord et al. | 607/2 |
| 6,029,086 A | 2/2000 | Kim et al. | 607/9 |
| 6,031,710 A | 2/2000 | Wolf et al. | 361/302 |
| 6,063,034 A | 5/2000 | Doten et al. | 600/448 |
| 6,068,589 A | 5/2000 | Neukermans | 600/25 |
| 6,070,097 A | 5/2000 | Kreger et al. | 600/521 |
| 6,112,119 A * | 8/2000 | Schuelke et al. | 607/9 |
| 6,195,585 B1 | 2/2001 | Karunasiri et al. | 607/57 |
| 6,198,968 B1 | 3/2001 | Prutchi et al. | 607/9 |
| 6,201,993 B1 | 3/2001 | Kruse et al. | 607/30 |
| 6,208,900 B1 | 3/2001 | Ecker et al. | 607/17 |
| 6,223,083 B1 | 4/2001 | Rosar | 607/60 |
| 6,230,059 B1 | 5/2001 | Duffin | 607/60 |
| 6,236,882 B1 | 5/2001 | Lee et al. | 600/509 |
| 6,272,381 B1 | 8/2001 | Callaghan et al. | 607/26 |
| 6,282,446 B1 | 8/2001 | Eberle et al. | 607/5 |
| 6,321,115 B1 | 11/2001 | Mouchawar et al. | 607/9 |
| 6,421,554 B1 * | 7/2002 | Lee et al. | 600/509 |
| 2003/0087371 A1 | 5/2003 | Palreddy et al. | 607/28 |
| 2004/0106957 A1 * | 6/2004 | Palreddy et al. | 607/9 |

* cited by examiner

CARDIAC RHYTHM MANAGEMENT SYSTEM WITH NOISE DETECTOR UTILIZING A HYSTERESIS PROVIDING THRESHOLD

TECHNICAL FIELD

This document relates generally to cardiac rhythm management systems, devices, and methods, and particularly, but not by way of limitation, to a cardiac rhythm management system with a noise detector that reduces the likelihood that noise on a cardiac signal is erroneously sensed as a cardiac depolarization.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poorly spatially-coordinated heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency. Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem faced by cardiac rhythm management devices is in detecting the atrial and/or ventricular depolarizations in the intrinsic electrical cardiac signals, since the delivery of therapy to the heart is typically based at least in part on the timing and/or morphology of such detected depolarizations. To detect a depolarization event, the cardiac signal may be amplified, filtered, and/or level-detected (e.g., to determine whether an artifact exceeds a particular threshold level associated with an atrial or ventricular depolarization). Depolarization detection is complicated, however, by the fact that the intrinsic cardiac signals may include noise unrelated to the heart depolarization. The noise may arise from a variety of sources, including, among other things: myopotentials associated with skeletal muscle contractions; a loose or fractured leadwire providing intermittent contact between the device and the heart; or, electromagnetic interference from AC power provided to nearby electrical equipment (e.g., 60 Hertz), from nearby switching power supplies, from a nearby electrosurgical tool, from communication equipment, or from electronic surveillance equipment. Noise erroneously detected as a heart depolarization may inappropriately inhibit bradyarrhythmia pacing therapy or cardiac resynchronization therapy, or may inappropriately trigger tachyarrhythmia shock therapy. For these reasons, the present inventor has recognized a need for detecting the presence of such noise, and using this information in such a way that the occurrence of such consequences can be reduced or avoided altogether.

SUMMARY

This document discusses, among other things, a system, method, or device that determines whether noise is present on a sampled and/or digitized sensed intrinsic cardiac signal based on a moving count of turning/inflection points of the signal. If noise is detected, the manner in which the cardiac signal is acquired, or the manner in which the device operates in response to the acquired cardiac signal (or both) is altered to reduce the risk of erroneously detecting noise as a heart depolarization and, therefore, inappropriately triggering or withholding therapy.

In one example, this document discusses a method of determining whether a sampled cardiac signal is noisy. The method includes determining whether an evaluation sample of the cardiac signal is a turning point with respect to previous and subsequent samples. A number of the turning points is counted over a predetermined plurality of cardiac samples. A window that includes the predetermined plurality of cardiac samples is deemed to be noisy if the number of turning points exceeds a threshold value.

In another example, this document discusses a system. The system includes a first electrode associated with a heart.

A cardiac signal detector is coupled to the first electrode. The cardiac signal detector includes a detector output providing a sampled cardiac signal. A signal processor circuit determines, over a predetermined plurality of cardiac signal samples, whether an evaluation sample of the cardiac signal is a turning point with respect to previous and subsequent samples. The signal processor circuit deems a portion of the cardiac signal to be noisy if a number of turning points exceeds a threshold value for the predetermined plurality of cardiac signal samples. Other aspects of the invention will be apparent on reading the following detailed description of the invention and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
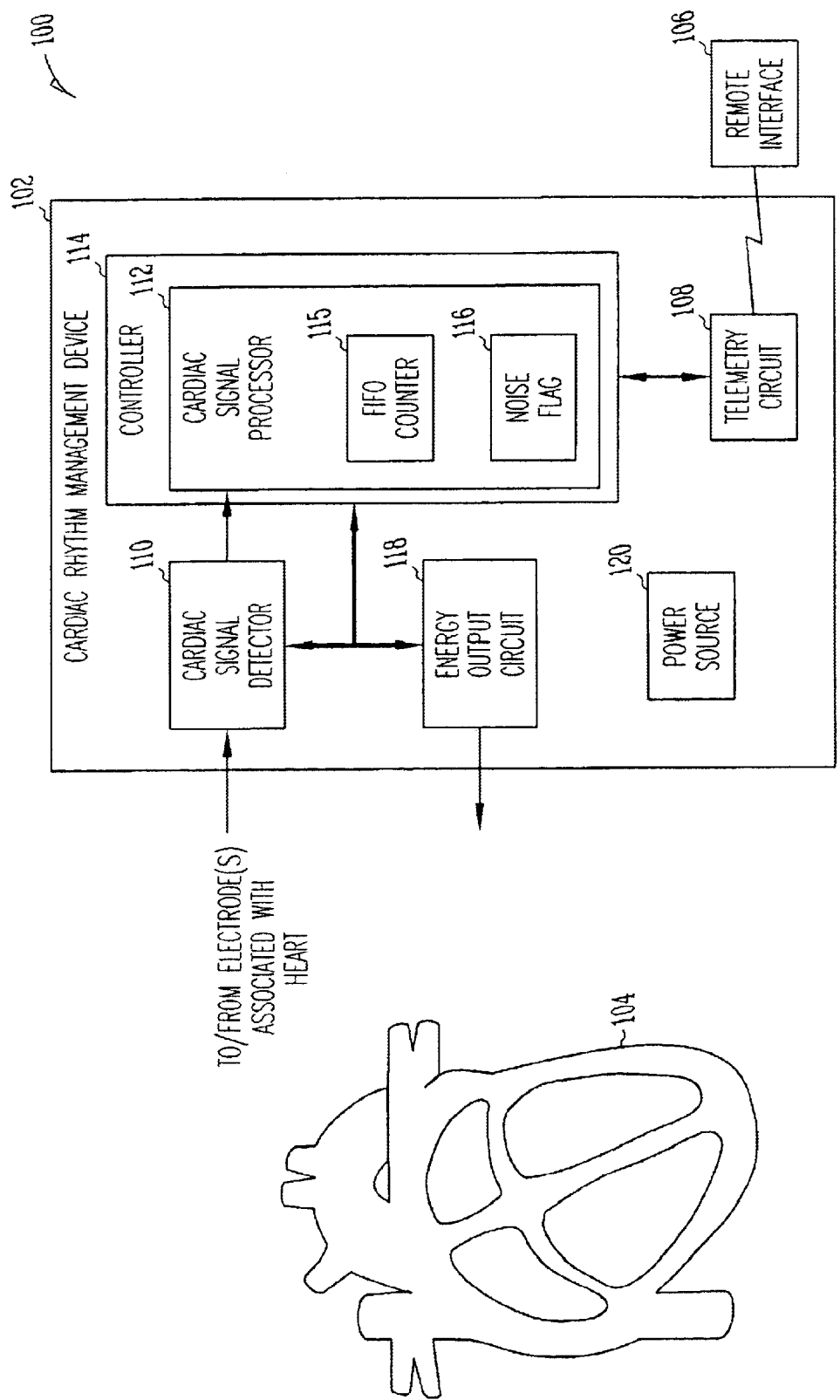
FIG. 1 is a block diagram illustrating generally portions of a cardiac rhythm management system and portions of an environment in which it is used.

FIG. 1 is a block diagram illustrating generally portions of a cardiac rhythm management system 100 and portions of an environment in which it is used. In this example, system 100 includes a cardiac rhythm management device 102 coupled to a heart 104 by one or more electrodes associated with heart 104, such as for sensing intrinsic cardiac signals and/or for delivering energy or other therapy to heart 104. System 100 also includes a programmer or other remote interface 106, which is wirelessly or otherwise communicatively coupled to a telemetry circuit 108 or other communication circuit in device 102. Device 102 includes a pacer, a defibrillator, a cardiac resynchronization therapy (CRT) device, a monitor, a device that combines more than one of these functions, or any other implantable or external device for diagnosing and/or treating the heart. In one example, device 102 is sized and shaped for being pectorally or abdominally implanted in a human patient. The electrode(s) coupling device 102 to heart 104 may include an intravascular electrode, an intracardiac electrode, an epicardial electrode, or a housing or a header electrode located on a housing of device 102 or a header attached thereto, or any combination of the above. In some configurations, such as where portion(s) of device 102 are external to the patient, the electrode(s) coupling device 102 to heart 104 may include a skin surface electrode external to the patient. The electrodes may be associated with the heart for bipolar (i.e., two electrodes that are relatively close together) or for unipolar (i.e., two electrodes that are farther apart) signal sensing or therapy energy delivery (e.g., pacing pulse or shocks).

In the example of FIG. 1, device 102 includes a cardiac signal detector 110 having an input coupled to heart 104 by electrodes associated with heart 104 in a suitable manner for sensing an intrinsic cardiac signal. Detector 110 need not actually extract heart depolarizations from the sensed intrinsic cardiac signal; such functions may be performed elsewhere in device 102. Detector 110 typically includes a sense amplifier for acquiring and amplifying the cardiac signal. Detector 110 may also include one or more continuous-time and/or discrete time (e.g., switched-capacitor) filter circuits, such as for selectively emphasizing the desired heart depolarization information relative to other acquired signal content. Detector 110 may also include an analog-to-digital converter (ADC) to convert continuous-time and/or discrete time samples into numerical representations of those samples. Detector 110 may also include one or more digital filters (or other digital signal processing circuitry) following the ADC, such as for selectively emphasizing the desired heart depolarization information relative to other acquired signal content. Detector 110 also includes an output providing a periodically sampled data cardiac signal x(n) to a cardiac signal processor module 112 of controller 114. Controller 114 is capable of sequencing through various control states such as, for example, by using a digital microprocessor having executable instructions stored in an associated instruction memory circuit, a microsequencer, or a state machine. In operation, by executing these instructions, controller 114 provides the functionality of cardiac signal processor module 112, as well as providing control signals to cardiac signal detector 110 and an energy output circuit 118. In one example, cardiac signal processor module 112 includes a first-in-first-out (FIFO) memory and counter 115 and a noise flag 116 (such as, for example, a bit in a register) to assist in the noise detection technique discussed herein. Energy output circuit 118 provides pacing or resynchronization pulses, defibrillation shocks, or other appropriate cardiac therapy to heart 104. Device 102 also includes a battery or other power source 120.

Figure 2:
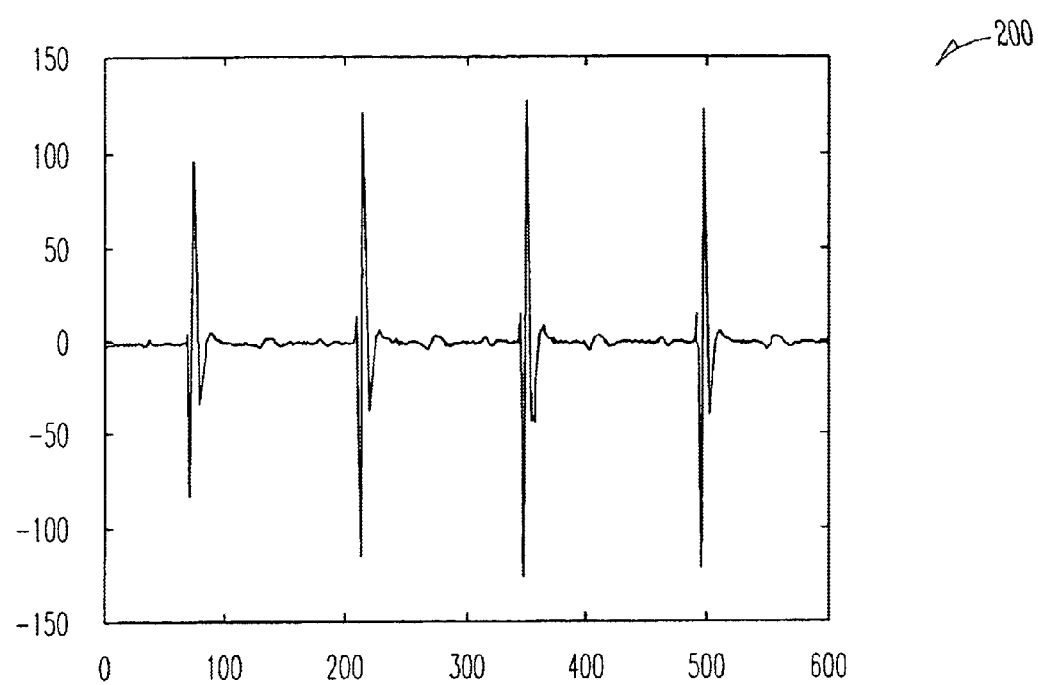
FIG. 2 is a graph illustrating generally a relatively noise-free cardiac signal.
Figure 3:
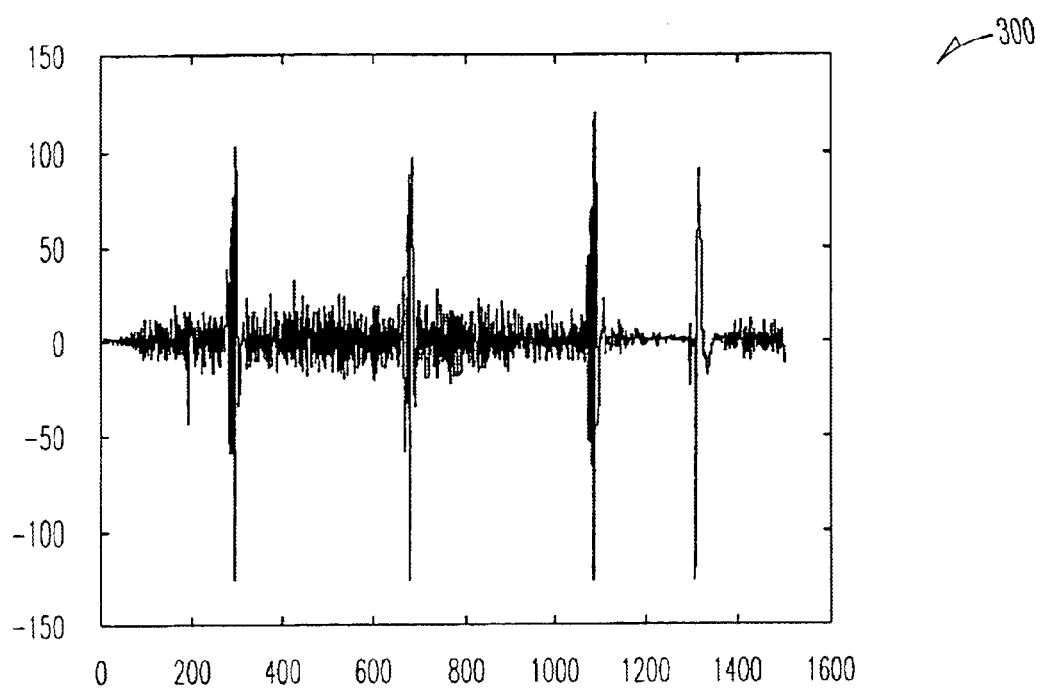
FIG. 3 is a graph illustrating generally a relatively noisy cardiac signal.

FIG. 2 is a graph illustrating generally a relatively noise-free cardiac signal 200 obtained from electrodes associated with heart 104. FIG. 3 is a graph illustrating generally a relatively noisy cardiac signal 300 similarly obtained from electrodes associated with heart 104. In the example of FIG. 3, the additional noise may make the underlying heart chamber depolarizations difficult to detect, since the noise may include frequencies within the passband of the depolarizations and may, therefore, erroneously be level-detected as an actual heart depolarization.

Figure 4:
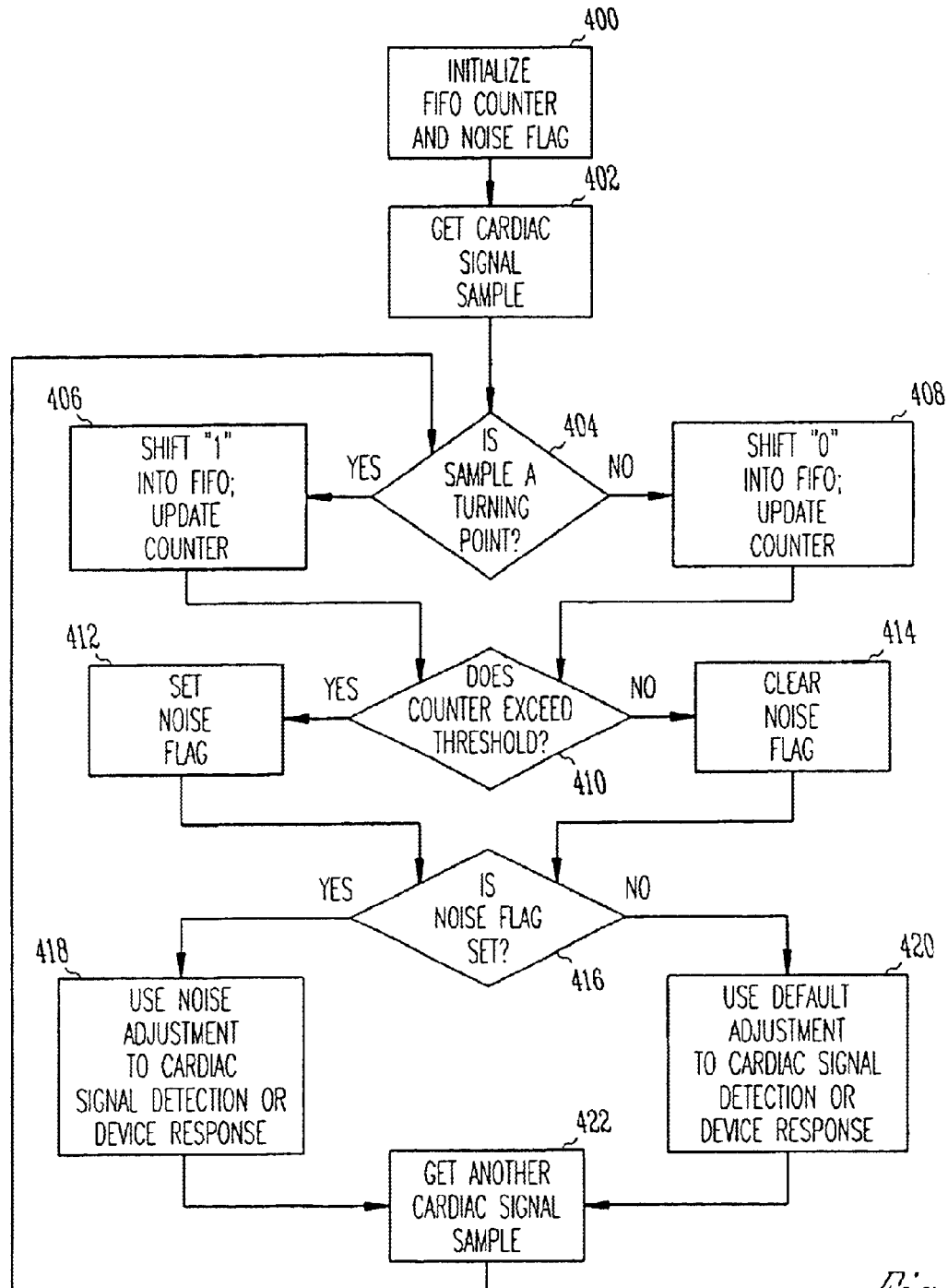
FIG. 4 is a flow chart illustrating generally one example of a noise detection technique.

FIG. 4 is a flow chart illustrating generally one example of a noise detection technique performed by cardiac signal processor 112 on the sampled cardiac signal x(n) that is output by cardiac signal detector 110. At 400, FIFO counter 115 and noise flag 116 are initialized. In one example, FIFO counter 115 includes an N-bit shift register, which is initialized at 400 to all zeros, and also includes an associated counter that outputs a sum of the number of ones in the N-bit shift register. Noise flag 116 is also initialized to zero, indicating that noise has not yet been detected as being present on the cardiac signal x(n). At 402, a cardiac signal sample is obtained. At 404, a previously-obtained evaluation sample is considered as to whether it represents a turning point (also referred to as an inflection point), with respect to a cardiac signal sample previous to the evaluation sample, and with respect to a cardiac signal sample subsequent to the evaluation sample. If, at 404, the evaluation sample is deemed a turning point, then at 406, a logic "1" is shifted into the N-bit FIFO shift register, the earliest-stored bit in the shift register is discarded, and FIFO counter 115 is then updated to represent the new sum of the number of ones in the N-bit shift register. Otherwise, where the evaluation sample is not deemed a turning point, then at 408 a logic "0" is shifted into the N-bit shift register, the earliest stored bit in the shift register is discarded, and FIFO counter 115 is updated to represent the new sum of the number of ones in the N-bit shift register. After 406 or 408, at 410, the sum of the ones in the N-bit shift register provided by FIFO counter 115 is compared to a predetermined threshold value. If the sum exceeds the predetermined threshold value, then at 412 the noise flag is set to indicate that noise is present on the sampled cardiac signal x(n) obtained from cardiac signal detector 110. Otherwise, where the sum does not exceed the predetermined threshold value, then at 414 the noise flag is cleared to indicate that noise is not present on the sampled cardiac signal x(n) obtained from cardiac signal detector 110. After 412 or 414, at 416, the noise flag is evaluated to determine whether noise is present on the sampled cardiac signal x(n), as indicated by the noise flag being set. If the cardiac signal is noisy, then, at 418, one or more noise adjustment parameters and/or techniques is applied to the cardiac signal detection by cardiac signal detector 110 or to the response of device 102 to the acquired cardiac signal. Otherwise, where the cardiac signal is not noisy, then, at 420, one or more default parameters and/or techniques is applied to the cardiac signal detection by cardiac signal detector 110 or to the response of device 102 to the acquired cardiac signal. After 418 or 420, at 422, another cardiac signal sample is obtained by cardiac signal processor 112, so that another evaluation sample can be considered to determine whether the evaluation sample is a turning or inflection point, at 404. Additionally, device 102 may optionally communicate the state of the noise flag to an external programmer or other remote user interface 106 via telemetry circuit 108. Therefore, FIG. 4 illustrates, among other things, that a significant proportion of turning or inflection points in the sampled cardiac signal may indicate the presence of noise, which indication, in turn, may be used to modify the way in which the cardiac signal is obtained so as to reduce the likelihood that noise deflections are erroneously interpreted as heart depolarizations.

In the example FIG. 4, the counter may alternatively be compared to a multi-valued threshold, such as for providing hysteresis. In one such example, the threshold includes two distinct values: a majority threshold value and a quorum threshold value. The majority threshold value typically exceeds the quorum threshold value. At 400, the threshold is set to the higher majority value. At 412, upon setting the noise flag, the threshold is then set to the lower quorum value. At 414, upon clearing the noise flag, the threshold is then set to the higher majority value. In operation, once the counter exceeds the majority value, the threshold is then decreased to the quorum value. This effectively adds hysteresis to reduce or avoid chatter around the quorum threshold value.

Figure 5:
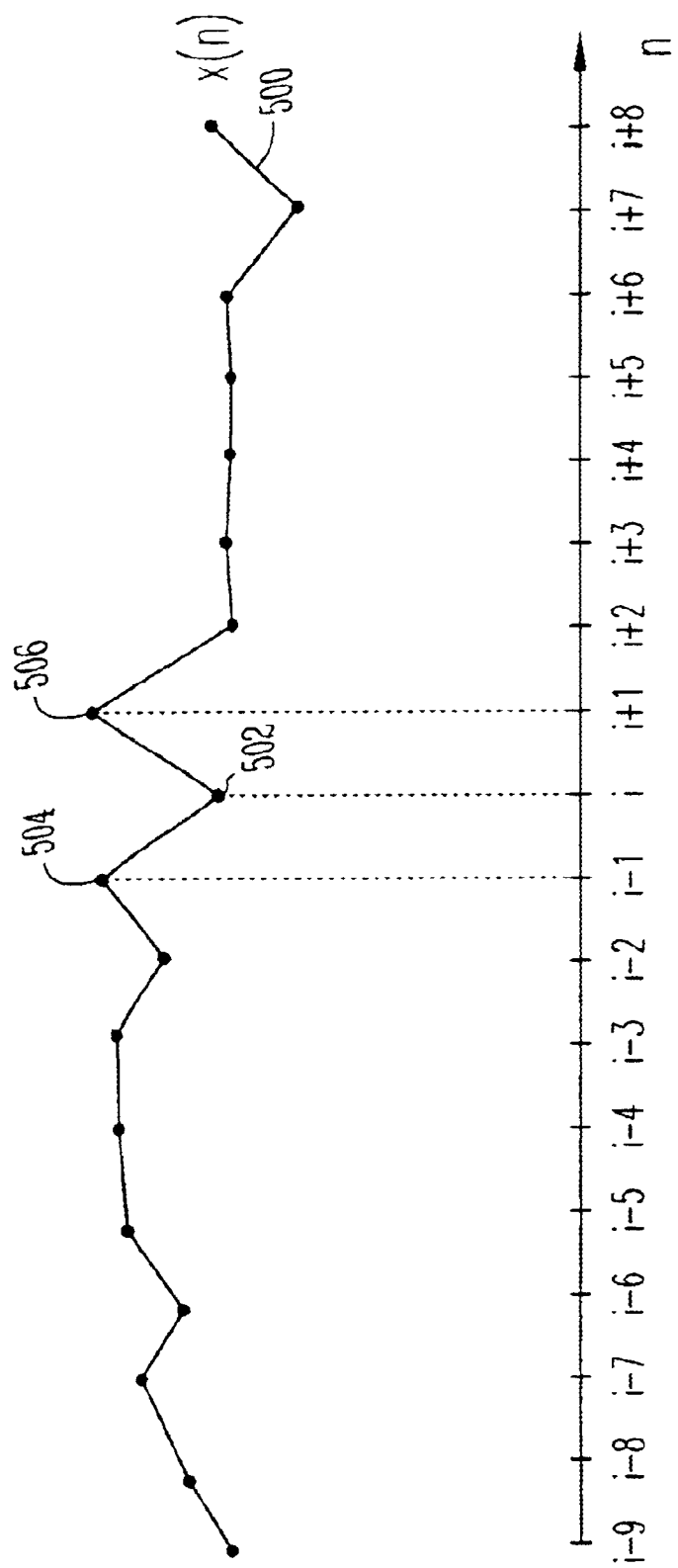
FIG. 5 is a signal graph of a sampled cardiac signal, illustrating generally one technique for determining whether an evaluation sample is a turning/inflection point.

FIG. 5 is a signal graph of a sampled cardiac signal 500, illustrating generally one technique for determining (such as performed at 404 of FIG. 4) whether an evaluation sample 502 is a turning or inflection point. In this example, the presence of noise is determined from: the evaluation sample 502, x(i); a previous sample 504, such as immediately preceding sample x(i−1); and a subsequent sample 506, such as immediately succeeding sample x(i+1). In this example, using the three samples, x(i), x(i−1), and x(i+1), the following equation is evaluated:

$$TP = \text{sign}\{x(i)-x(i-1)\} * \text{sign}\{x(i+1)-x(i)\} \tag{1}$$

Equation 1 illustrates taking the sign of a first difference x(i)−x(i−1). A negative sign represents a negative-going signal excursion between the i sample and the (i−1) sample. A positive sign represents a positive-going signal excursion therebetween. Equation 1 also illustrates taking the sign of a second difference x(i+1)−x(i). A negative sign represents a negative going signal excursion between the (i+1) sample and the i sample. A positive sign represents a positive-going signal excursion therebetween. Thus, the product of the signs of the first and second differences, TP, will be −1 whenever the signal excursions on either side of the evaluation sample x(i) differ in direction or sense of their slopes, in which case the evaluation sample x(i) represents a turning/inflection point. Evaluation of the three samples then is shifted rightward on the signal illustration of FIG. 5, such as when another cardiac signal sample is obtained at 422 of FIG. 4, so that the number of turning/inflection points in a sliding window preceding the evaluation sample x(i) can be counted and compared to a threshold to determine whether a sufficient number of turning points has been detected to deem the cardiac signal to be noisy.

In the above example, choice of the x(i), x(i−1), and x(i+1) samples is simply a matter of convenience for ease of illustration of the above turning point noise detection technique. In particular, this example is not intended to imply a noncausal system. The above-discussed technique (or the other techniques discussed in this document) also applies to any other choice of sequential samples such as, for example, x(i), x(i−1), and x(i−2), or alternatively, x(i−1), x(i−2), and x(i−3), etc.

In a slightly modified example, a threshold requirement is added to the above technique for determining whether an evaluation sample 502 is a turning or inflection point. The threshold determines a noise floor below which the noise detection is substantially no longer sensitive. In one such example, a TP is evaluated according to Equation 1, but if $|x(i)-x(i-1)|<TH_1$, or if $|x(i+1)-x(i)|<TH_2$, then TP is set to a value different from−1 (e.g., set to 1) to indicate that evaluation sample 502 is not a turning point. $TH_1$ and $TH_2$ may take on the same, or different, threshold values. In one example, $TH_1=TH_2=2$ counts of an 8-bit A/D converter signal representing the sampled cardiac signal x(n). This suppresses excessive sensitivity to noise occurring at or beneath the level of 1 least significant bit (LSB). A similar threshold requirement may also be imposed on the other turning point evaluation techniques discussed in this document.

In one example, TP is a binary-valued signal that is high ("1") if the evaluation sample 502 is a turning point, and low ("0") otherwise. In another example, TP is a tri-state signal that is "−1" if the evaluation sample 502 is an inflection point, "0" if the slopes on either side of evaluation sample 502 are too small to determine whether evaluation sample 502 is an inflection point, and "1" if the slopes on either side of evaluation sample 502 are the same sign, such that evaluation sample 502 is not a turning point.

Figure 6:
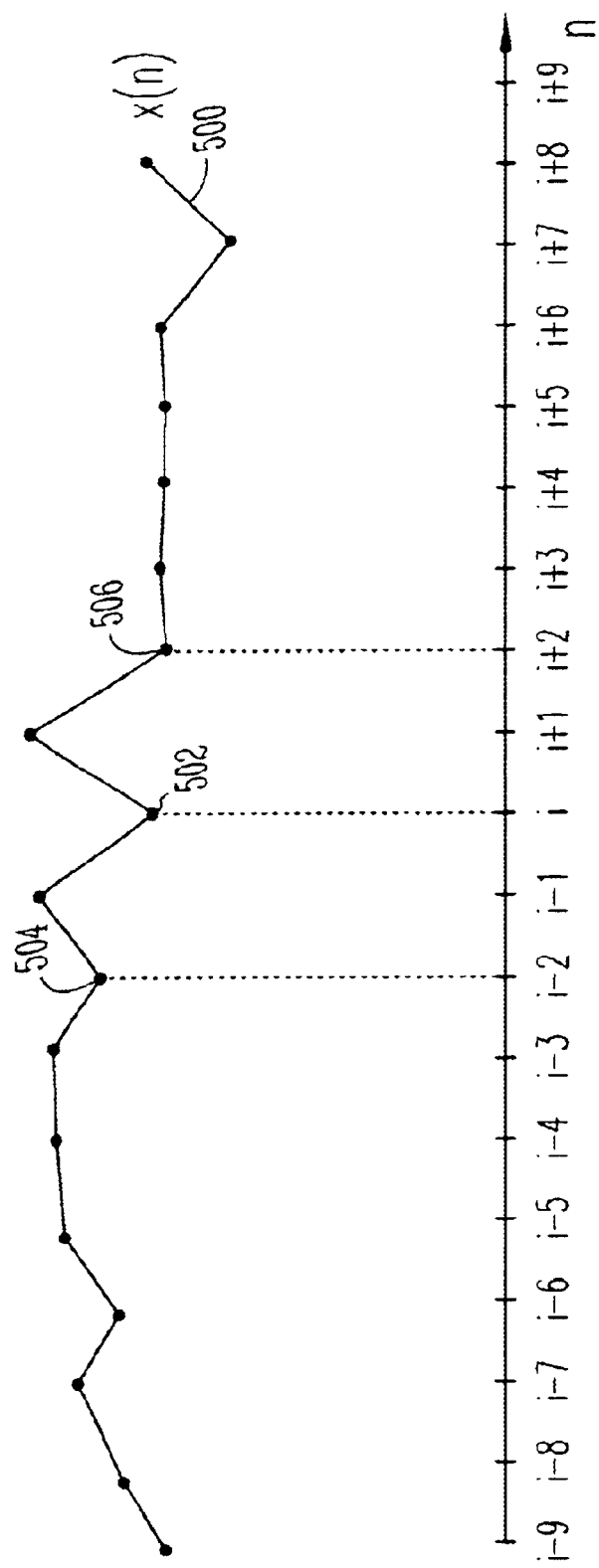
FIG. 6 is a signal graph of the sampled cardiac signal of FIG. 5, illustrating, among other things, that the turning/inflection point evaluation may be performed at a different frequency from that at which the cardiac signal was sampled.

FIG. 6 is a signal graph of the sampled cardiac signal 500 of FIG. 5, illustrating that the turning/inflection point evaluation need not be performed at the same frequency at which the cardiac signal was sampled. In the example of FIG. 6, the turning/inflection point determination is based on the evaluation sample 502, x(i); a previous sample 504, such as preceding sample x(i−2); and a subsequent sample 506, such as succeeding sample x(i+2). Thus, Equation 1 can be expressed more generally as:

$$TP=\text{sign}\{x(i)-x(i-K1)\}*\text{sign}\{x(i+K2)-x(i)\} \quad (2)$$

where K1 and K2 are integer offset constants which may, but need not, be the same value. Moreover, the turning point evaluation may be carried out repeatedly over different subsampling frequencies of the frequency at which the cardiac signal was sampled. In such a technique, a vector of TP values corresponding to the different subsampling frequencies may provide useful information about the frequency content of the noise, or may allow the noise detection to be tailored to noise having a particular frequency content. In one example, this is accomplished by varying K between different values, and, at the different values of K: (1) determining, for each sample, $TP=\text{sign}\{x(i)-x(i-K)\}*\text{sign}\{x(i+K)-x(i)\}$, in which x(i) is the ith sample of the sampled cardiac signal x(n), and in which K is an integer offset, and in which TP=−1 is used as at least one factor indicating that x(i) is a turning point: and (2) deeming the cardiac signal to be noisy if a number of turning points occurring during a fixed number of samples preceding x(i) exceeds a threshold value.

Figure 7:
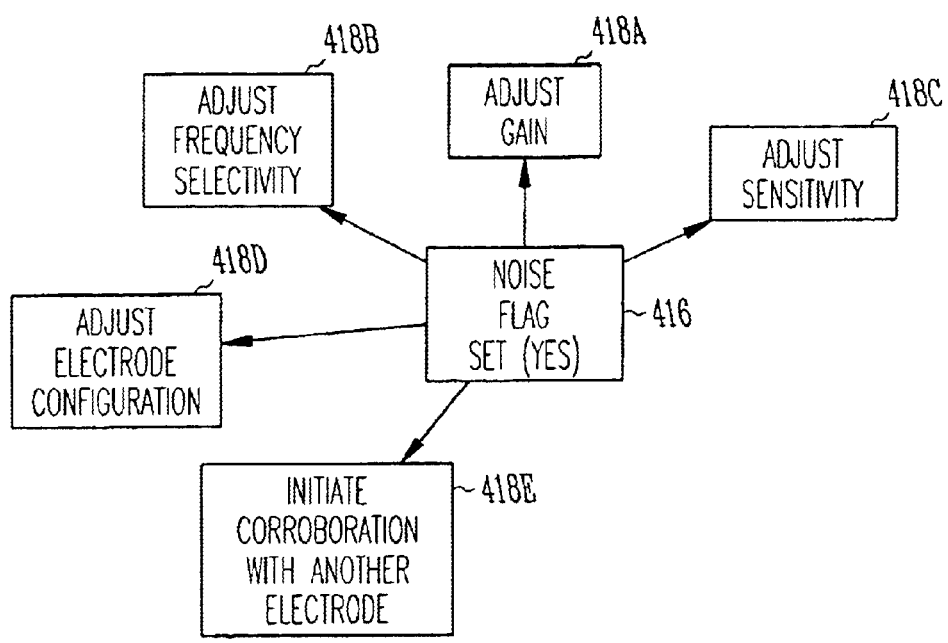
FIG. 7 is a block diagram illustrating generally, by way of example, but not by way of limitation, several possible operational adjustments that may be performed in response to a noisy cardiac signal.

FIG. 7 is a block diagram illustrating generally, by way of example, but not by way of limitation, several possible operational adjustments that may be performed by device 102 at 418 of FIG. 4 in response to noise flag 116 being set as determined at 416 of FIG. 4. In one example, at 418A, a sense amplifier gain in cardiac signal detector 110 is adjusted (e.g., decreased) when noise is present to avoid erroneously detecting the noise as a heart depolarization. For example, in a switched-capacitor sense amplifier, controller 114 provides a control signal to cardiac signal detector 110 to use different gain-setting switched-capacitors. This noise-dependent gain adjustment effectively uses noise detection as input to an automatic gain control (AGC) feedback system. In an alternative example, at 418B, a frequency selectivity characteristic of the sense amplifier or other cardiac signal filter is adjusted when cardiac signal noise is present to increase the selectivity to the heart depolarization frequencies of interest and more aggressively discriminate against noise at nearby higher or lower frequencies. Alternatively, at 418C, a sensitivity is adjusted (e.g., decreased) in the presence of cardiac signal noise. This may be accomplished, for example, by raising a level-detector threshold for heart depolarizations. Alternatively, at 418D, a sensing electrode configuration is adjusted. For example, where first and second pairs of bipolar sensing electrodes are associated with the same heart chamber, and the first pair of sensing electrodes yields a noisy signal, cardiac signal detector 110 may be decoupled from the first pair of sensing electrodes and coupled instead to the second pair of sensing electrodes in order to try to obtain a less noisy signal. This may be effective, for example, for noise resulting from a fractured lead or other poor connection between the first pair of sensing electrodes and cardiac signal detector 110. In other examples, the sensing electrode configuration may be switched from unipolar sensing to bipolar sensing or vice-versa. In an alternative example, at 418E, noise present on a first electrode pair, for example, may trigger corroboration of heart depolarization detection with an independent second sensing channel that is coupled to a second heart electrode pair. In this example, a heart depolarization detected at the first electrode pair by a first cardiac signal detector would require verification as also having been detected at the second electrode pair by a second cardiac signal detector, thereby reducing the system's susceptibility to erroneously detecting noise as a heart depolarization and thereby inappropriately triggering or withholding therapy to heart 104.

The above noise detection techniques were tested on data acquired from a human heart from electrodes configured for bipolar sensing. The resulting intrinsic cardiac signal was amplified by a high input impedance continuous-time amplifier and a switched-capacitor discrete-time sense amplifier. Filtering was performed to remove frequencies outside of the range of about 20 Hz to about 130 Hz. The resulting sampled cardiac signal was provided at a sampling frequency of about 200 Hz. The above-described noise detection technique was used in which the turning/inflection points were determined from an evaluation sample, an immediately preceding sample, and an immediately succeeding sample. A moving window (e.g., FIFO shift-register length) of N=10 samples was used. A threshold value of 4 turning/inflection points in the N=10 samples was taken to indicate the presence of noise on the cardiac signal. The results showed good discrimination between the cardiac signal noise and a true fine ventricular fibrillation waveform, which should be sensed as true ventricular heart depolarizations rather than noise.

Figure 8:
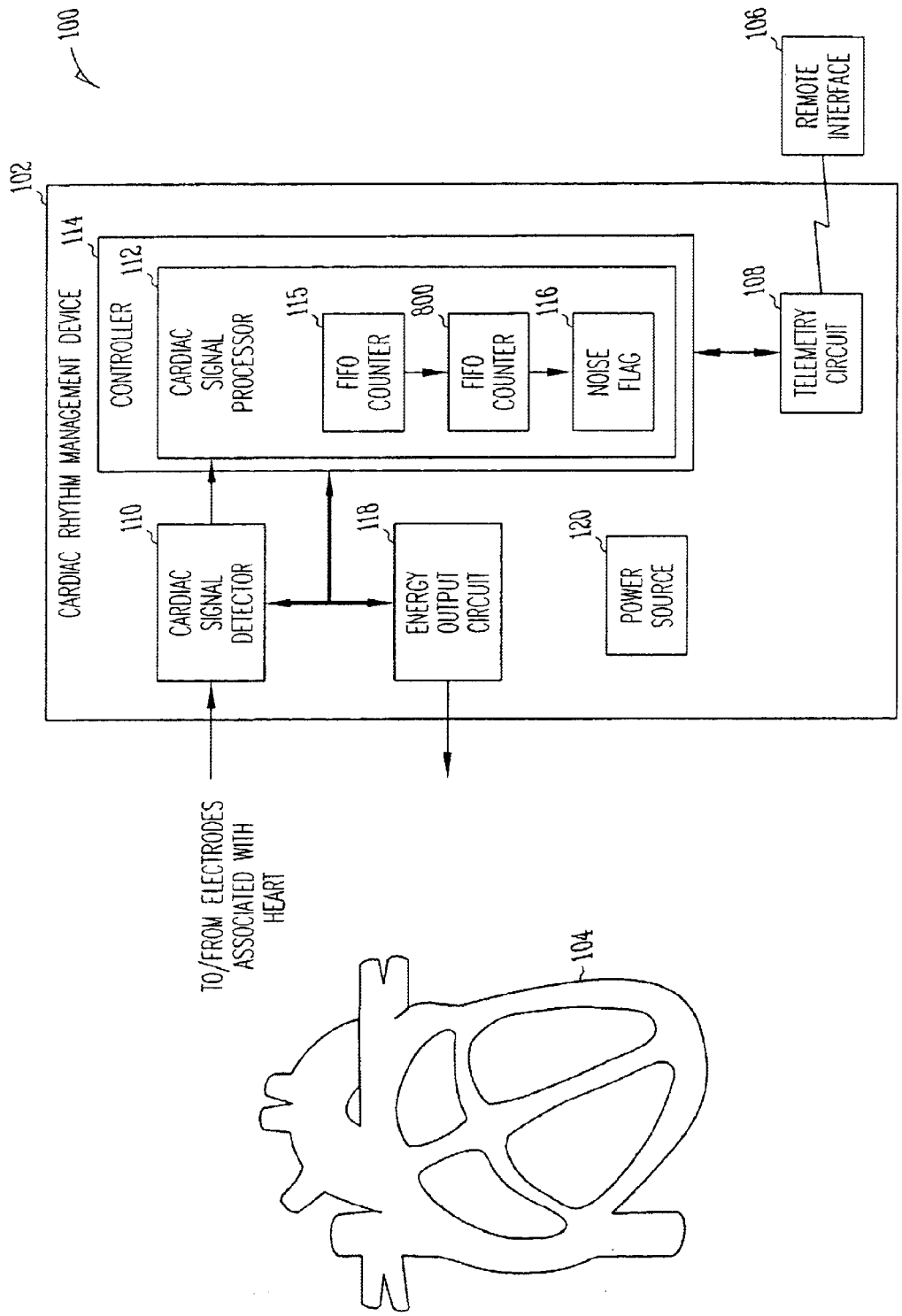
FIG. 8 is a block diagram illustrating an alternative example of a system including a second FIFO counter for performing the noise detection technique illustrated in the flow chart of FIG. 9.
Figure 9:
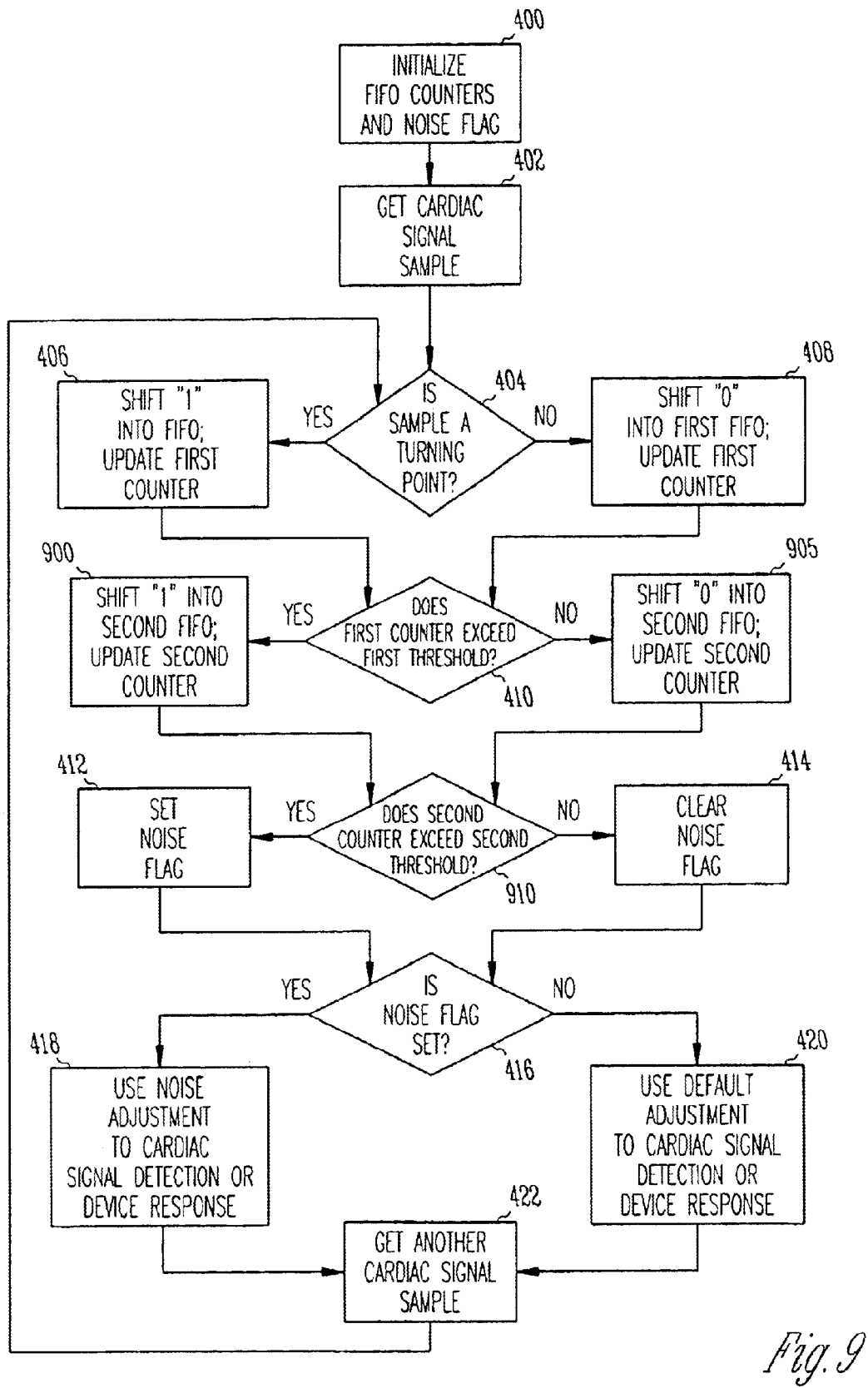
FIG. 9 is a flow chart illustrating generally another example of a noise detection technique.

FIG. 8 is a block diagram illustrating an alternative example of a system 100 in which device 102 includes a second FIFO counter 800 for performing the noise detection technique illustrated in the flow chart of FIG. 9. In FIG. 9, which shares certain similarities with FIG. 4, first FIFO counter 115, a second FIFO counter 800, and noise flag 116 are initialized. In one example, first FIFO counter 115 includes an N-bit shift register, which is initialized at 400 to all zeros, and also includes an associated first counter that outputs a sum of the number of ones in the N-bit shift register. In this example, second FIFO counter 800 includes an M-bit shift register, which is initialized at 400 to all zeros, and also includes an associated second counter that outputs a sum of the number of ones in the M-bit shift register. Noise flag 116 is also initialized to zero, indicating that noise has not yet been detected as being present on the cardiac signal x(n).

At 402, a cardiac signal sample is obtained. At 404, a previously-obtained evaluation sample is considered as to whether it represents a turning point (also referred to as an inflection point), with respect to a cardiac signal sample previous to the evaluation sample, and with respect to a cardiac signal sample subsequent to the evaluation sample. If, at 404, the evaluation sample is deemed a turning point, then at 406, a logic "1" is shifted into the N-bit first FIFO shift register, the earliest-stored bit in the shift register is discarded, and first FIFO counter 115 is then updated to represent the new sum of the number of ones in the N-bit shift register. Otherwise, where the evaluation sample is not deemed a turning point, then at 408 a logic "0" is shifted into the N-bit shift register, the earliest stored bit in the shift register is discarded, and first FIFO counter 115 is updated to represent the new sum of the number of ones in the N-bit shift register.

After 406 or 408, at 410, the sum of the ones in the N-bit shift register provided by first FIFO counter 115 is compared to a first predetermined threshold value. If the sum exceeds the predetermined threshold value, then at 900 a logic "1" is shifted into the M-bit second FIFO shift register, the earliest-stored bit in the shift register is discarded, and second FIFO counter 800 is then updated to represent the new sum of the number of ones in the M-bit shift register. Otherwise, where the evaluation sample is not deemed a turning point, then at 905 a logic "0" is shifted into the M-bit shift register, the earliest stored bit in the shift register is discarded, and second FIFO counter 800 is updated to represent the new sum of the number of ones in the M-bit shift register. After 900 or 905, at 910, the sum of the ones in the M-bit shift register provided by second FIFO counter 800 is compared to a second predetermined threshold value, which may be different than the first predetermined threshold value. If the sum exceeds the second predetermined threshold value, then at 412 the noise flag is set to indicate that noise is present on the sampled cardiac signal x(n) obtained from cardiac signal detector 110. Otherwise, where the sum does not exceed the predetermined threshold value, then at 414 the noise flag is cleared to indicate that noise is not present on the sampled cardiac signal x(n) obtained from cardiac signal detector 110.

After 412 or 414, at 416, the noise flag is evaluated to determine whether noise is present on the sampled cardiac signal x(n), as indicated by the noise flag being set. If the cardiac signal is noisy, then, at 418, one or more noise adjustment parameters and/or techniques is applied to the cardiac signal detection by cardiac signal detector 110 or to the response of device 102 to the acquired cardiac signal. Otherwise, where the cardiac signal is not noisy, then, at 420, one or more default parameters and/or techniques is applied to the cardiac signal detection by cardiac signal detector 110 or to the response of device 102 to the acquired cardiac signal. After 418 or 420, at 422, another cardiac signal sample is obtained by cardiac signal processor 112, so that another evaluation sample can be considered to determine whether the evaluation sample is a turning or inflection point, at 404. Additionally, device 102 may optionally communicate the state of the noise flag to an external programmer or other remote user interface 106 via telemetry circuit 108. Therefore, FIG. 9 illustrates, among other things, an example in which the output of the N-bit shift register indicates whether a particular "window" is noisy, and the output of the M-bit shift register indicates whether a predetermined number of "windows" is noisy, such that the signal should be deemed noisy. FIGS. 4 and 9 illustrate the process of cascading additional windows, together with corresponding counters and thresholds. This process can be extended to cascading any number of additional windows, as needed.

As discussed above with respect to FIG. 4, the first and second counters may alternatively be compared to respective multi-valued thresholds, such as for providing hysteresis. In one such example, each of the first and second thresholds includes two distinct values: a majority threshold value and a quorum threshold value. The majority threshold value typically exceeds its corresponding quorum threshold value. At 400, the first threshold is set to its higher majority value, and the second threshold is likewise set to its higher majority value. At 900, if the first counter exceeds the first threshold, the first threshold is then set to its lower quorum value. At 905, if the first counter does not exceed the first threshold, then the first threshold is then set to the higher majority value. At 412, upon setting the noise flag, the second threshold is then set to its lower quorum value. At 414, upon clearing the noise flag, the second threshold is then set to its higher majority value. In operation, once each counter exceeds its majority value, its threshold is then decreased to its quorum value. This effectively adds hysteresis to reduce or avoid chatter around the respective quorum threshold values.

Figure 10:
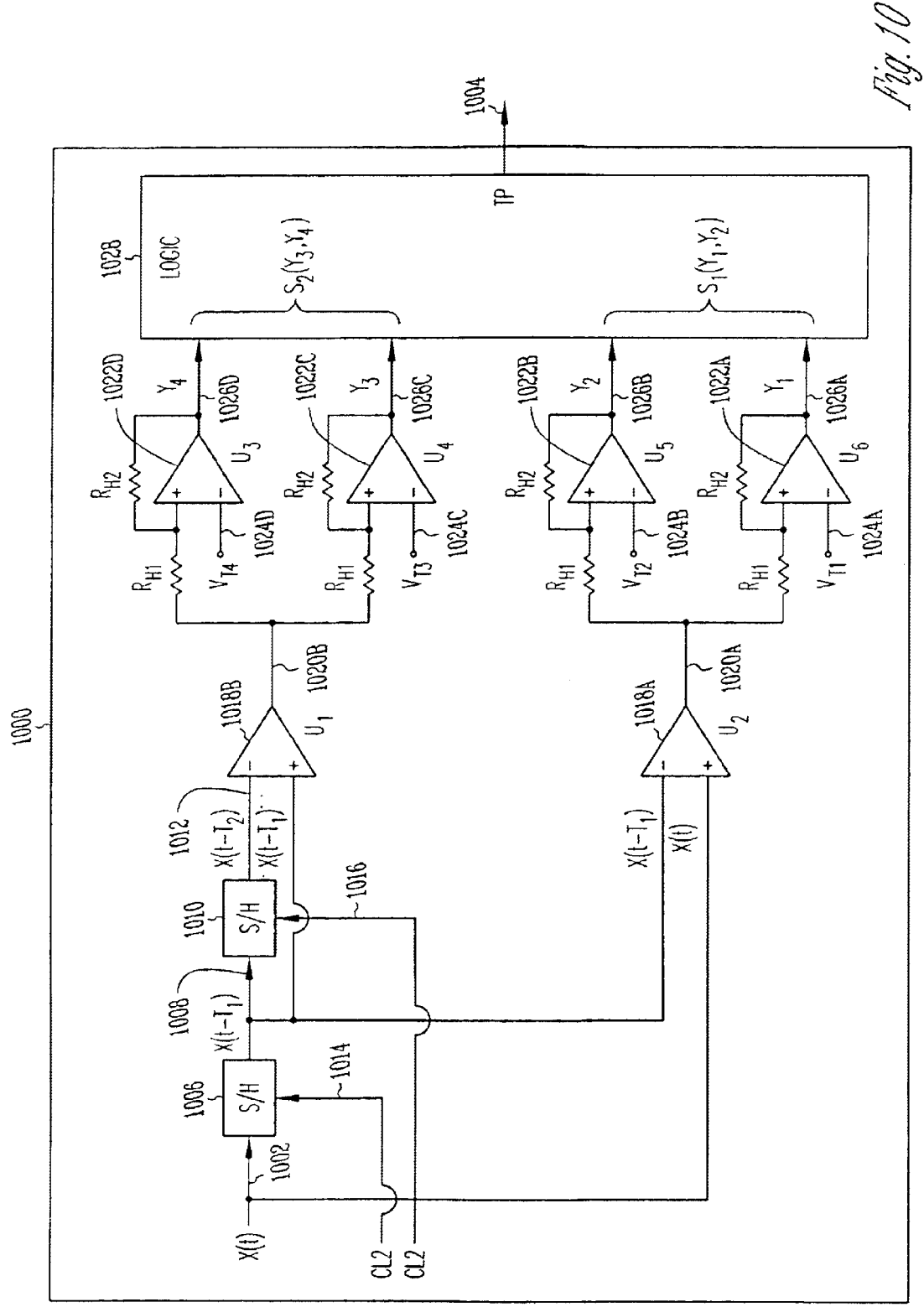
FIG. 10 is a schematic/block diagram illustrating generally one example of a turning point detector for operating upon an analog acquired cardiac signal x(t) and providing an indication of whether a particular sample of the acquired cardiac signal x(t) represents a turning point in the acquired cardiac signal x(t).

FIG. 10 is a schematic/block diagram illustrating generally one example of a turning point detector 1000, suitable for being included within cardiac signal detector 110, for operating upon an analog acquired cardiac signal x(t) at input node 1002 and providing an indication TP at output node 1004 of whether a particular sample of the acquired cardiac signal x(t) represents a turning point in the acquired cardiac signal x(t). In the example of FIG. 10, the acquired continuous time cardiac signal x(t) is input to a first sample-and-hold (S/H) circuit 1006, to create a delayed sample $x(t-T_1)$ output at node 1008. This, in turn is input to a second S/H 1010, to create a further delayed sample $x(t-T_2)$ at node 1012. The appropriate delay is obtained by clocking S/H circuits 1006 and 1010 by one or more appropriately timed clock signals, such as CL1 and CL2 received at clocking input nodes 1014 and 1016 of S/H 1006 and S/H 1010, respectively.

The samples x(t), $x(t-T_1)$, and $x(t-T_2)$ are received at inputs of differential amplifiers/buffers 1018A–B, which may provide gain greater than one, unity gain, or attenuation, as appropriate. In this example, $x(t-T_1)$ is received at a negative input of amplifier 1018A and at a positive input of amplifier 1018B, x(t) is received at a positive input of amplifier 1018A, and $x(t-T_2)$ is received at a negative input of amplifier 1018B. Amplifier 1018A provides an output representing the difference $[x(t)-x(t-T_1)]$ at node 1020A to first and second comparators 1022A–B. Amplifier 1018B provides an output representing the difference $[x(t-T_1)-x(t-T_2)]$ at node 1020B to third and fourth comparators 1022C–D.

Each of comparators 1022A–D also receive a reference voltage input. For example, comparator 1022A receives at node 1024A a reference voltage $V_{T1}$, comparator 1022B receives at node 1024B a reference voltage $V_{T2}$, comparator 1022C receives at node 1024C a reference voltage $V_{T3}$, and comparator 1022D receives at node 1024D a reference voltage $V_{T4}$. In this example, $V_{T1}$, $V_{T3}$ are slightly negative voltages, and $V_{T2}$, $V_{T4}$ are slightly positive voltages.

In this example, comparator 1022A outputs a binary-valued signal $Y_1$ at node 1026A that is high when the difference $[x(t)-x(t-T_1)]>V_{T1}$ and low otherwise, comparator 1022B outputs a binary-valued signal $Y_2$ at node 1026B that is high when the difference $[x(t)-x(t-T_1)]>V_{T2}$ and low otherwise, comparator 1022C outputs a binary-valued signal $Y_3$ at node 1026C that is high when the difference $[x(t-T_1)-x(t-T_2)]>V_{T3}$ and low otherwise, and comparator 1022D outputs a binary-valued signal $Y_4$ at node 1026D that is high when the difference $[x(t-T_1)-x(t-T_2)]>V_{T4}$ and low otherwise.

The signals Y1, Y2, Y3, and Y4 are input to digital logic circuit 1028, which outputs the binary valued signal TP at node 1004 that is high when $x(t-T_1)$ represents a turning point with respect to $x(t)$ and $x(t-T_2)$. In one example, logic circuit 1028 is configured to implement functionality based on a double-bit signal $S_1$, comprised of signals $Y_1$ and $Y_2$, and another double-bit signal $S_2$, comprised of signals $Y_3$ and $Y_4$. The signal $S_1$ includes information about the slope of the difference $[x(t)-x(t-T_1)]$, and the signal $S_2$ includes information about the slope of the difference $[x(t-T_1)-x(t-T_2)]$, as described more particularly below in Tables 1 and 2.

TABLE 1

| | Definition of $S_1$ | |
|---|---|---|
| $S_1$ | $Y_2 = 0$ (Low) | $Y_2 = 0$ (High) |
| $Y_1 = 0$ (Low) | A | D |
| $Y_1 = 1$ (High) | B | C |

TABLE 2

| | Definition of $S_2$ | |
|---|---|---|
| $S_2$ | $Y_4 = 0$ (Low) | $Y_4 = 1$ (High) |
| $Y_3 = 0$ (Low) | A | D |
| $Y_3 = 1$ (High) | B | C |

In Tables 1 and 2, A represents a negative slope, B represents a small absolute slope, C represents a positive slope, and D is not a valid state. The digital logic for providing the output TP is defined by Table 3. As seen in Table 3, TP is high when the difference $[x(t)-x(t-T_1)]$ represents a negative slope and the difference $[x(t-T_1)-x(t-T_2)]$ represents a positive slope, or vice-versa, and is low otherwise (the "X" notation refers to invalid states, which may be considered as "don't care" for the purposes of logical minimization for realization of the logic circuit).

TABLE 3

| | Definition of TP | | | |
|---|---|---|---|---|
| TP | $S_2 = A$ | $S_2 = B$ | $S_2 = C$ | $S_2 = D$ |
| $S_1 = A$ | 0 | 0 | 1 | X |
| $S_1 = B$ | 0 | 0 | 0 | X |
| $S_1 = C$ | 1 | 0 | 0 | X |
| $S_1 = D$ | X | X | X | X |

Figure 11:
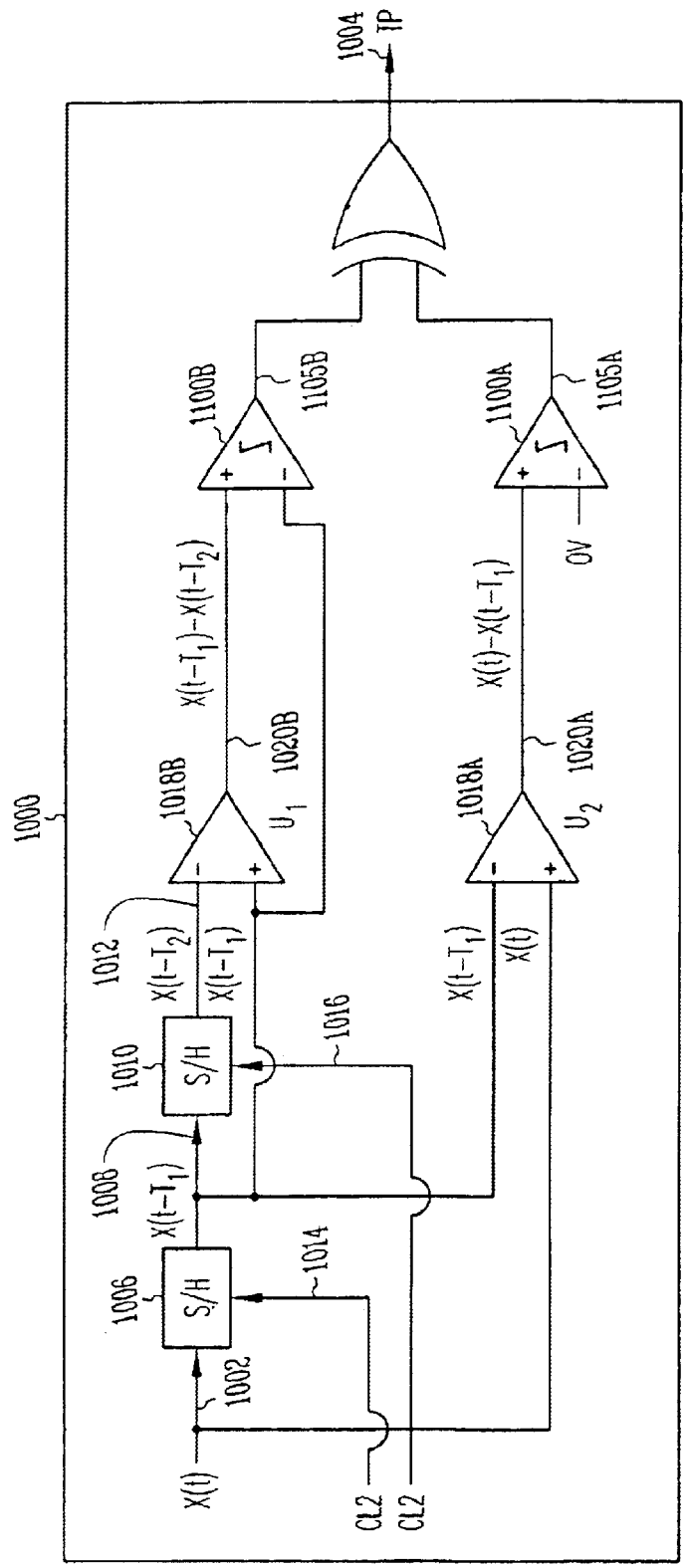
FIG. 11 is a schematic/block diagram illustrating generally another example of a turning point detector for operating upon an analog acquired cardiac signal x(t) and providing an indication of whether a particular sample of the acquired cardiac signal x(t) represents a turning point in the acquired cardiac signal x(t).

Although the configuration of comparators 1022A–D in FIG. 10 effectively implements a window comparator that will not yield a turning point if the slopes of either the difference $[x(t)-x(t-T_1)]$ or the difference $[x(t-T_1)-x(t-T_2)]$ is of small magnitude, such a threshold requirement on the slopes is not required. For example, FIG. 11 is a schematic/block diagram illustrating generally an example in which these differences are each compared to 0V, by respective comparators 1100A–B. The respective comparator outputs at nodes 1105A–B are input to an exclusive-OR (XOR) gate 1110. XOR gate 1110 outputs TP, which is high when the sign of the difference $[x(t)-x(t-T_1)]$ is different from that of the difference $[x(t-T_1)-x(t-T_2)]$.

It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method of determining whether a sampled cardiac signal is noisy, the method including:
   determining whether an evaluation sample of the cardiac signal is a turning point with respect to previous and subsequent samples;
   counting a number of the turning points over a predetermined plurality of cardiac samples; and
   deeming a window that includes the predetermined plurality of cardiac samples to be noisy if the number of turning points exceeds a threshold value, in which the threshold value includes a majority threshold value and a quorum threshold value.

2. The method of claim 1, in which the determining whether the evaluation sample of the cardiac signal is a turning point includes:
   determining first and second directions of the cardiac signal preceding an following the evaluation sample, respectively; and
   deeming the evaluation sample to be a turning point if the first direction is different from the second direction.

3. The method of claim 2, further including deeming the evaluation sample to be other than a turning point if at least one of the first and second directions manifests a slope of a magnitude that is less than a threshold value.

4. The method of claim 1, in which the determining whether the evaluation sample is a turning point is carried out at a frequency that is different from a sampling frequency.

5. The method of claim 1, further including setting a noise flag if the window is deemed noisy.

6. The method of claim 5, further including changing the threshold value from the majority threshold value to the quorum threshold value upon the setting the noise flag.

7. The method of claim 5, in which the majority threshold value is a larger magnitude than the quorum threshold value.

8. The method of claim 1, further including, if the cardiac signal is deemed noisy, at least one of:
   adjusting a detecting of the cardiac signal; and
   adjusting a response to the detecting of the cardiac signal.

9. The method of claim 1, in which the previous sample is taken at a first predetermined number of periodic samples away from the evaluation sample and the subsequent sample is taken at a second predetermined number of periodic samples away from the evaluation sample.

10. The method of claim 9, in which the first and second predetermined number are equal.

11. The method of claim 9, in which the first and second predetermined number are varied over a range.

12. The method of claim 1, in which the previous and subsequent samples respectively immediately precede and immediately succeed the evaluation sample.

13. The method of claim 1, further including:

counting a number of windows deemed noisy; and setting a noise flag if the number of windows deemed noisy exceeds a window threshold value.

14. The method of claim 1, further including clearing a noise flag.

15. The method of claim 14, further including establishing the threshold value at the majority threshold value upon the clearing the noise flag.

16. The method of claim 15, in which the majority threshold value is a larger magnitude than the quorum threshold value.

17. A method including:

(a) detecting a cardiac signal from electrodes associated with a heart;

(b) sampling the cardiac signal periodically to obtain a sampled cardiac signal $x(n)$;

(c) determining, for each sample, TP=sign $\{x(i)-x(i-K)\}$*sign$\{x(i+K)-x(i)\}$, in which $x(i)$ is the ith sample of the sampled cardiac signal $x(n)$, and in which K is an integer offset, and in which TP=−1 is used as at least one factor indicating that $x(i)$ is a turning point; and (d) deeming the cardiac signal to be noisy if a number of turning points occurring during a fixed number of samples preceding $x(i)$ exceeds a threshold value, in which the threshold value includes a majority threshold value and a quorum threshold value.

18. The method of claim 17, in which if $|x(i)-x(i-K)|$ is less than a first threshold or $|x(i+K)-x(i)|$ is less than a second threshold, then $x(i)$ is deemed to be not a turning point.

19. The method of claim 17, in which K=1.

20. The method of claim 17, further including varying K between different values, and carrying out (c) and (d) at the different values, of K.

21. The method of claim 17, further including setting a noise flag if the window is deemed noisy.

22. The method of claim 17, further including, if the cardiac signal is deemed noisy, at least one of:

adjusting the detecting the cardiac signal; and adjusting a response to the detecting the cardiac signal.

23. The method of claim 22, in which the adjusting the detecting the cardiac signal includes at least one of adjusting a gain, adjusting a sensitivity threshold, adjusting a frequency selectivity, switching an electrode from which the cardiac signal is sensed, and corroborating sensed depolarizations with another cardiac signal detected from a different electrode.

24. A method of determining whether a sampled cardiac signal is noisy, the method including:

determining whether an evaluation sample of the cardiac signal is a turning point with respect to previous and subsequent samples;

counting a number of the turning points over a predetermined plurality of cardiac samples; and deeming a window that includes the predetermined plurality of cardiac samples to be noisy if the number of turning points exceeds a threshold value, in which the threshold value includes a first threshold value and a second threshold value, wherein the first threshold value is of larger magnitude than the second threshold value;

setting a noise flag if the window is deemed noisy;

clearing the noise flag if the window is deemed not noisy;

setting the threshold value at the first threshold value upon setting the noise flag; and setting the threshold value at the second threshold value upon clearing the noise flag.

25. A method including:

detecting a cardiac signal from electrodes associated with a heart;

sampling the cardiac signal periodically to obtain a sampled cardiac sign $x(n)$;

determining, for each sample, TP=sign $\{x(i)-x(i-K)\}$*sign$\{x(i+K)-x(i)\}$, n which $x(i)$ is the ith sample of the sampled cardiac signal $x(n)$, and in which K is an integer of set, and in which TP=−1 is used as at least one factor indicating that $x(i)$ is a turning point; and deeming the cardiac signal to be noisy if a number of turning points occurring during a fixed number of samples preceding $x(i)$ exceeds a threshold value, in which the threshold value includes a first threshold value and a second threshold value, wherein the first threshold value is of larger magnitude than the second threshold value;

setting a noise flag if the window is deemed noisy;

clearing the noise flag if the window is deemed not noisy;

setting the threshold value at the first threshold value upon setting the noise flag; and setting the threshold value at the second threshold value upon clearing the noise flag.

26. A method of determining whether a sampled cardiac signal is noisy, the method including:

determining whether an evaluation sample of the cardiac signal is a turning point with respect to previous and subsequent samples;

counting a number of the turning points over a predetermined plurality of cardiac samples; and deeming a window that includes the predetermined plurality of cardiac samples to be noisy if the number of turning points exceeds a threshold value that provides hysteresis.

27. A method including:

detecting a cardiac signal from electrodes associated with a heart;

sampling the cardiac signal periodically to obtain a sampled cardiac signal $x(n)$;

determining, for each sample, TP=sign $\{x(i)-x(i-K)\}$*sign$\{x(i+K)-x(i)\}$, n which $x(i)$ is the ith sample of the sampled cardiac signal $x(n)$, and in which K is an integer offset, and in which TP=−1 is used as at least one factor indicating that $x(i)$ is a turning point; and deeming the cardiac signal to be noisy if a number of turning points occurring during a fixed number of samples preceding $x(i)$ exceeds a threshold value that provide hysteresis.

* * * * *

UNITED STATES PATENT AND TRADEMARK OFFICE
CERTIFICATE OF CORRECTION

PATENT NO. : 6,892,092 B2
APPLICATION NO. : 10/046650
DATED : May 10, 2005
INVENTOR(S) : Palreddy et al.

It is certified that error appears in the above-identified patent and that said Letters Patent is hereby corrected as shown below:

In column 7, line 58, after "point" delete ":" and insert - - ; - -, therefor.

In column 12, line 40, in Claim 2, delete "an" and insert - - and - -, therefor.

In column 13, line 43, in Claim 20, after "values" delete ",".

In column 14, line 18, in Claim 25, delete "sign" and insert - - signal - -, therefor.

In column 14, line 20, in Claim 25, delete "n" and insert - - in - -, therefor.

In column 14, line 57, in Claim 27, delete "n" and insert - - in - -, therefor.

Signed and Sealed this

First Day of August, 2006

JON W. DUDAS
*Director of the United States Patent and Trademark Office*